US008759789B2

(12) United States Patent
Laitinen

(10) Patent No.: US 8,759,789 B2
(45) Date of Patent: Jun. 24, 2014

(54) BODY MODULE FOR AN OPTICAL MEASUREMENT INSTRUMENT

(75) Inventor: Jyrki Laitinen, Kuusisto (FI)

(73) Assignee: Wallac Oy, Turku (FI)

( * ) Notice: Subject to any disclaimer, the term of this patent is extended or adjusted under 35 U.S.C. 154(b) by 233 days.

(21) Appl. No.: 13/146,305

(22) PCT Filed: Jan. 18, 2010

(86) PCT No.: PCT/FI2010/050020
§ 371 (c)(1),
(2), (4) Date: Sep. 20, 2011

(87) PCT Pub. No.: WO2010/084243
PCT Pub. Date: Jul. 29, 2010

(65) Prior Publication Data
US 2012/0001089 A1    Jan. 5, 2012

Related U.S. Application Data

(60) Provisional application No. 61/149,544, filed on Feb. 3, 2009.

(30) Foreign Application Priority Data

Jan. 26, 2009   (FI) ...................................... 20095061

(51) Int. Cl.
G01J 1/58      (2006.01)
G21H 3/02      (2006.01)
G01N 1/10      (2006.01)

(52) U.S. Cl.
USPC ........................................ 250/458.1; 356/246

(58) Field of Classification Search
USPC ........................................ 250/458.1; 356/246
See application file for complete search history.

(56) References Cited

U.S. PATENT DOCUMENTS 3,628,386 A * 12/1971 Blum ............................ 74/89.14
4,311,358 A *  1/1982 Gibbons et al. ............... 359/385
(Continued)

FOREIGN PATENT DOCUMENTS

CN       1549921 A     11/2004
EP    0 523 521 A2      1/1993
(Continued)

OTHER PUBLICATIONS

International Search Report, dated Apr. 26, 2010, from corresponding PCT application.

(Continued)

Primary Examiner — David Porta
Assistant Examiner — Jeremy S Valentiner
(74) Attorney, Agent, or Firm — Young & Thompson

(57) ABSTRACT

A body module of an optical measurement instrument includes: a reception device (201) for receiving samples, a first plate (202), a second plate (203) substantially parallel with the first plate and movably supported relative to the first plate in a direction perpendicular to the first and second plates, and walls extending from outer edges of the first plate to outer edges of the second plate. The reception device is located in a measurement chamber constituted by the walls and the first and second plates. At least the second plate includes a fastening interface provided with an aperture. The fastening interface is suitable for an optical module to be mounted to the second plate. The measuring chamber provides protection against undesired stray light from surroundings. The movability of the second plate allows adjustment of a distance between a sample and an optical module mounted to the second plate.

13 Claims, 5 Drawing Sheets

(56) References Cited

U.S. PATENT DOCUMENTS

| | | | |
|---|---|---|---|
| 5,290,513 | A | 3/1994 | Berthold et al. |
| 6,977,722 | B2 | 12/2005 | Wohlstadter et al. |
| 7,842,246 | B2 | 11/2010 | Wohlstadter et al. |
| 2004/0057870 | A1* | 3/2004 | Isaksson et al. ............... 422/52 |
| 2006/0051251 | A1* | 3/2006 | Desrosiers et al. ........... 422/102 |
| 2008/0252966 | A1* | 10/2008 | Karaki .......................... 359/391 |

FOREIGN PATENT DOCUMENTS

| | | | |
|---|---|---|---|
| EP | 0 760 478 | A2 | 3/1997 |
| EP | 760478 | A2 * | 3/1997 |
| EP | 0 987 540 | A2 | 3/2000 |
| EP | 1 400 801 | A1 | 3/2004 |
| GB | 722 967 | A | 2/1955 |
| JP | S638537 | A | 1/1988 |
| JP | H10300660 | A | 11/1998 |
| JP | 11316186 | A | 11/1999 |
| JP | 2007010500 | A | 1/2007 |
| JP | 2008512666 | A | 4/2008 |
| WO | 00/04364 | A2 | 1/2000 |
| WO | 2005111587 | A1 | 11/2005 |
| WO | 2006027406 | A1 | 3/2006 |

OTHER PUBLICATIONS

Finnish Search Report, dated Aug. 21, 2009, from corresponding Finnish application.
Translation of Chinese Office Action, dated Mar. 28, 2013, from corresponding CN application.

* cited by examiner

BODY MODULE FOR AN OPTICAL MEASUREMENT INSTRUMENT

FIELD OF THE INVENTION

The invention relates to a body module for an optical measurement instrument. The body module can be used as a platform with the aid of which different optical measurement instruments can be constructed using different optical modules that may include for example lenses, fibres, detectors, light sources, etc. An optical measurement can be, for example but not necessarily, an absorption measurement, a photoluminescence measurement, or a chemiluminescence measurement. Furthermore, the invention relates to an optical measurement instrument.

BACKGROUND

The work in analytical biochemical laboratories and in clinical laboratories is often based on different tags or labels coupled on macromolecules under inspection. Typical labels used are different radioactive isotopes, enzymes, different fluorescent molecules and e.g. fluorescent chelates of rare earth metals. Detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances can be measured with absorption measurement, i.e. photometric measurement. In the absorption measurement the intensity of filtered and stabilized beam is first measured without any sample and then the sample inside one plate is measured. The absorbance i.e. the absorption values are then calculated.

The fluorescent substances can be measured with fluorescent measurement that is generally used for measuring quantities of fluorescent label substance in a sample. Most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus a photoluminometer suitable for photoluminescence measurements can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with a suitable wavelength e.g. 680 nm. After this, the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are sufficiently close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

An optical measurement instrument suitable for performing some or all of the measurements of the kind described above comprises typically at least one excitation light source for producing excitation beams to one or more samples to be measured at each time. Each excitation light source can be for example a flash lamp or a laser source. An optical path from an excitation light source to a sample may contain for example lenses, fibers, mirrors, dichroic mirrors, optical filters, monochromators and/or other optical elements. The optical measurement instrument further comprises at least one detector for detecting emission beams emitted by the samples to be measured at each time, and for producing detection signals responsive to the detected emission beams. Each detector can be for example a photo-diode or a photo-multiplier tube. An optical path from the sample to the detector may contain for example lenses, fibers, mirrors, dichroic mirrors, optical filters, monochromators, and/or other optical elements. The optical measurement instrument may further comprise a processing device for producing a measurement result for each sample to be measured on the basis of the detection signal related to that sample.

The optical measurement instrument comprises a reception device for receiving samples to be measured. Each sample to be measured is stored in one of a plurality of sample wells that are built on e.g. a microtitration plate or some other sample support element. The reception device can be, for example, a movable sledge adapted to receive the microtitration plate or the other sample support element. Due to the fact that the reception device allows moving the microtitration plate or the other sample support element, the samples can be measured in a temporally successive manner so that each sample is in turn the sample that is currently being measured. In order to provide appropriate optical measurements, a distance between a sample being measured and an optical module used as a measurement head has to be adjusted with a sufficient accuracy. Furthermore, the outer casing of the optical measurement instrument and/or other mechanical structures of it have to provide sufficient protection against undesired stray light and thermal radiation from the surroundings to the samples and to optical elements such as lenses, fibres, detectors, etc.

Publication U.S. Pat. No. 6,977,722 discloses an optical measurement instrument that includes an enclosure that is arranged to surround a reception device for receiving samples to be measured. The enclosure comprises a door element for enabling insertion of a microtitration plate or another sample support element into the enclosure. The enclosure constitutes a measurement chamber arranged to protect the samples to be measured against undesired stray light and thermal radiation from the surroundings. An upper surface of the enclosure is provided with an opening through which an end of an optical module such as a tube having successive lenses can be pushed into the vicinity of a sample being measured. The challenge related to the construction described above is that the interface between the enclosure and the optical module pushed into the opening of the enclosure should be sufficiently tight against stray light from the surroundings, and furthermore, allow adjustments of the distance between the end of the optical element and the sample being measured.

SUMMARY

In accordance with a first aspect of the invention, there is provided a new body module for an optical measurement instrument. The body module can be used as a platform with the aid of which different optical measurement instruments can be constructed using different optical modules that may include for example lenses, fibres, detectors, light sources, etc. A body module according to the invention comprises:

a first plate,
a second plate substantially parallel with the first plate and movably supported with respect to the first plate, the second plate being movable in a direction substantially perpendicular to the first and second plates and comprising at least one fastening interface provided with an aperture and being suitable for an optical module to be mounted to the second plate,
walls extending from outer edges of the first plate to outer edges of the second plate, the walls and the first and second plates constituting a measurement chamber and the walls comprising a door element for enabling insertion of samples to be measured into the measurement chamber, and
a reception device for receiving the samples to be measured, the reception device being located in the measurement chamber and being mechanically connected to a movable support rail so that the reception device is movable in a plane parallel with the first and second plates.

The walls between the first and second plates may comprise, for example, light impermeable flexible material that allows the second plate to move relative to the first plate, or, for another example, the walls may comprise overlapping portions arranged to slide relative to each other in response to movement of the second plate relative to the first plate.

As the second plate that represents one surface of the measurement chamber is movable in the above-described manner, the distance between an optical module mounted to the second plate and a sample to be measured can be adjusted so that there is no need to move the optical module relative to the second plate. Hence, it is easier to make the joint between the measurement chamber and the optical module tight against light than in conjunction with the optical measurement instrument according to the prior art described earlier in this document. It is also possible, but not necessary, to provide the first plate with at least one fastening interface suitable for an optical module to be mounted to the first plate.

In accordance with a second aspect of the invention, there is provided a new optical measurement instrument. An optical measurement instrument according to the invention comprises optical modules, at least one of the optical modules including an excitation light source arranged to produce an excitation beam for at least one of samples to be measured, at least one of the optical modules including a detector arranged to detect an emission beam emitted by one of the samples to be measured and to produce a detection signal responsive to the detected emission beam, and the optical measurement instrument further comprising a body module that comprises:

a first plate,
a second plate substantially parallel with the first plate and movably supported with respect to the first plate, the second plate being movable in a direction substantially perpendicular to the first and second plates and comprising at least one fastening interface provided with an aperture and being suitable for an optical module to be mounted to the second plate,
walls extending from outer edges of the first plate to outer edges of the second plate, the walls and the first and second plates constituting a measurement chamber and the walls comprising a door element for enabling insertion of samples to be measured into the measurement chamber, and
a reception device for receiving the samples to be measured, the reception device being located in the measurement chamber and being mechanically connected to a movable support rail so that the reception device is movable in a plane parallel with the first and second plates,
wherein at least one of the optical modules is mounted to the second plate of the body module via the fastening interface, the at least one optical module mounted to the second plate being at least one of the following: a part of a route of the excitation beam, a part of a route of the emission beam.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which:

FIG. 6b shows a schematic illustration of a view seen downwards from line A-A of FIG. 6a.

DESCRIPTION OF THE EMBODIMENTS

Figure 1A:
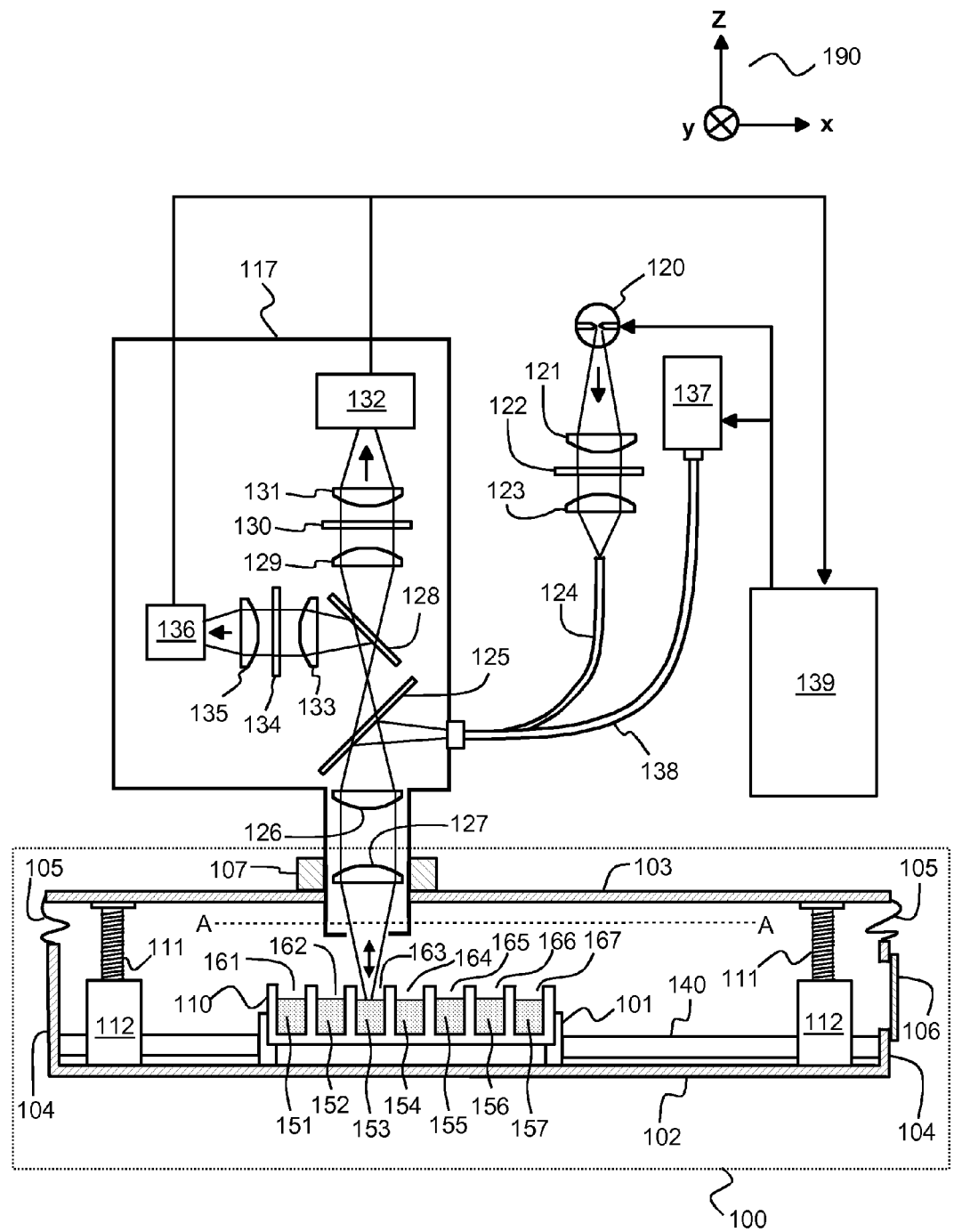
FIG. 1a shows a schematic illustration of a section view of an optical measurement instrument that comprises a body module according to an embodiment of the invention.

FIG. 1a shows a schematic illustration of a side view of an optical measurement instrument according to an embodiment of the invention. The optical measurement instrument comprises body module 100 that comprises a first plate 102 and a second plate 103 that is substantially parallel and, in a direction perpendicular to the first plate, overlapping with the first plate. The second plate 103 is movably supported with respect to the first plate 102 so that the second plate is movable in the direction substantially perpendicular to the first and second plates, i.e. the second plate is moveable in the positive and negative z-directions of the co-ordinate system 190. The second plate 103 is movably supported to the first plate 102 with threaded rods 111 and with respective counterparts 112. The counterparts can be provided for example with servomotors arranged to move the second plate 103 in the positive or negative z-direction. The body module comprises walls extending from outer edges of the first plate to outer edges of the second plate. The walls comprise a rigid portion 104 fastened to the outer edges of the first plate and a flexible portion 105 fastened between the rigid portion and the outer edges of the second plate. The flexible portion of the walls allows the movement of the second plate relative to the first plate. The walls and the first and second plates constitute a measurement chamber inside which there is a reception device 101 for receiving samples 151, 152, 153, 154, 155, 156, 157 to be measured. The measurement chamber constituted by the walls and the first and second plates is capable of protecting the samples against adverse stray light and thermal radiation from the surroundings. The walls comprise a door element 106 for enabling insertion of the samples to be measured into the measurement chamber. The second plate 103 comprises a fastening interface 107 provided with an aperture. The fastening interface is suitable for an optical module 117 that is mounted to the second plate 103. The distance between the optical module 117 and the sample being measured can be adjusted by moving the second plate 103 in the positive or negative z-direction.

Figure 1B:
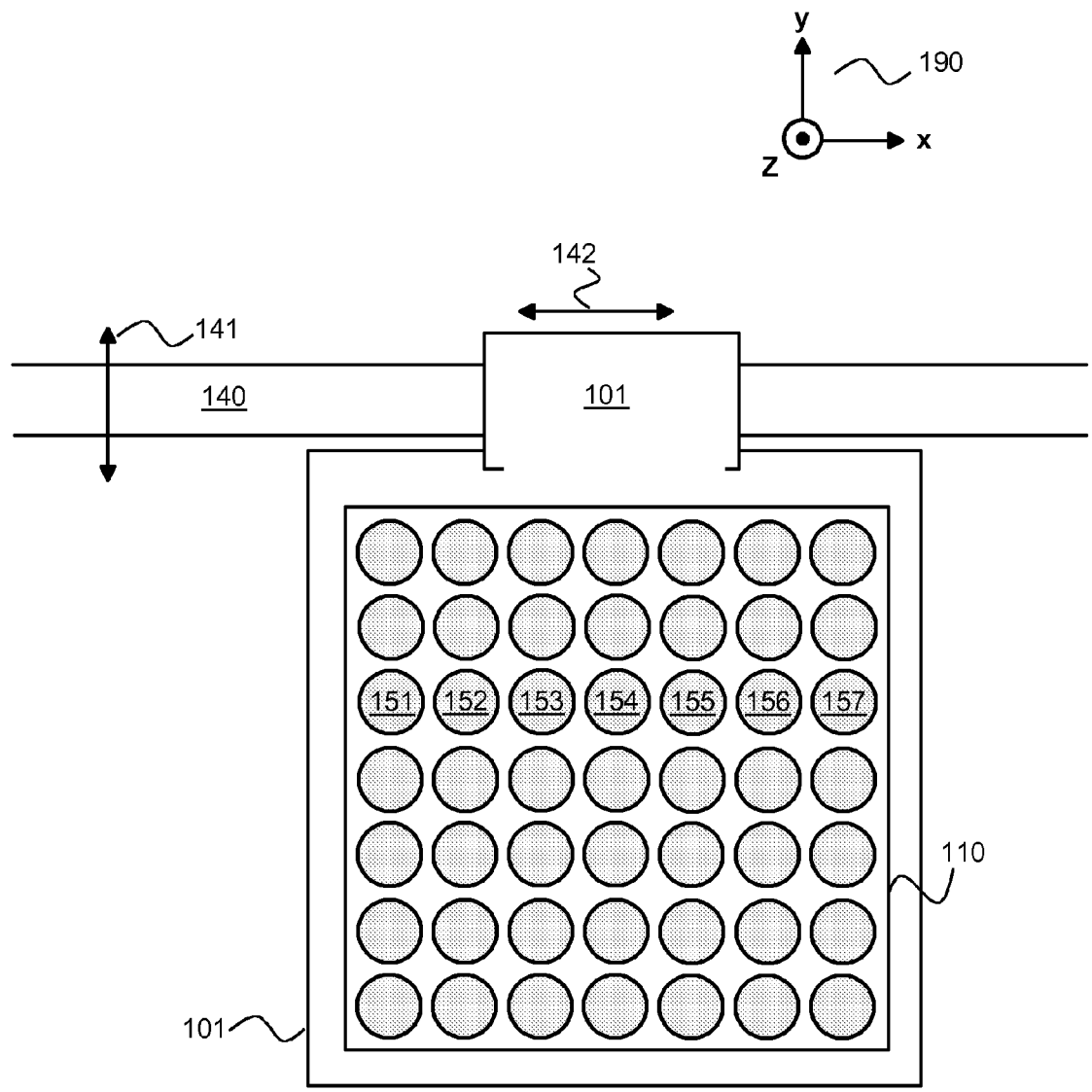
FIG. 1b shows a schematic illustration of a view seen downwards from line A-A of FIG. 1a, FIG. 2 shows a schematic illustration of a section view of an optical measurement instrument that comprises a body module according to an embodiment of the invention.

The samples 151, 152, 153, 154, 155, 156, 157 to be measured are stored in sample wells 161, 162, 163, 164, 165, 166, 167, respectively. FIG. 1b shows a schematic illustration of a view seen downwards from line A-A of FIG. 1a. As can be seen from FIG. 1b, the sample wells constitute in this exemplifying case a 7×7 array. In many cases there are, however, more sample wells in the array, e.g. 96 sample wells. The reception device 101 has an interface for receiving a changeable separate element 110, e.g. a microtitration plate, which includes the plurality of the sample wells. The reception device 101 is often called a sample plate sledge. The reception device 101 is mechanically connected to a support rail 140 that is movable in the directions defined by a two-headed arrow 141 shown in FIG. 1b. The reception device 101 is in turn movable along the support rail 140 in the directions defined by a two-headed arrow 142 shown in FIG. 1b. Hence, the reception device 101 and thus also the sample wells are movable in parallel with the first and second plates 102 and 103, i.e. the reception device 101 and the sample wells are movable in the xy-plane defined by the co-ordinate system 190. Thus, each sample can be measured in its turn by changing the mechanical position of the reception device 101. In the exemplifying situation shown in FIG. 1a, a sample that is currently being measured is the sample 153 that is stored in the sample well 163. In principle it would be possible that the element 110 including the sample wells is an integral part of the reception device, i.e. the reception device would comprise the sample wells, but several advantages are provided by having a changeable element that includes the plurality of sample wells.

Referring to FIG. 1a, the optical measurement instrument comprises an excitation light source 120 that is arranged to produce an excitation light beam. The excitation light source 120 can be, for example, a flash lamp. The excitation light beam radiated by the excitation light source 120 is collimated with a lens 121 and directed through an optical filter 122. Different optical filters can be selected for different wavelengths. The excitation light beam is then focused with a lens 123 to an end of a fibre optic guide 124, which guides the excitation light beam to the optical module 117. The fibre optic guide can be, for example, a bundle of fibres, such as 200 pieces of fibres with a diameter of e.g. 100 µm. The bundle of fibres can be used for mixing the excitation light beam in order to avoid an uneven distribution of light on a sample to be measured. The excitation light beam is reflected by a dichroic mirror 125 to a collimating lens 126. The excitation light beam is then focused with a lens 127 to the sample 153.

Photoluminescence emission beam from the sample 153 is directed with the lenses 127 and 126 to the dichroic mirror 125. The dichroic mirror is preferably designed so that it reflects excitation wavelength but transmits emission wavelengths. The emission beam is then divided into to two beams by a second mirror 128. The mirror 128 is preferably a dichroic mirror, which functions as a filter so that an emission beam with a first emission wavelength is transmitted through the mirror and an emission beam with a second emission wavelength is reflected by the mirror. The emission beam that is transmitted through the mirror 128 is collimated with a lens 129, filtered with an optical filter 130, and focused with a lens 131 into an aperture of a detector 132. The emission beam that is reflected by the mirror 128 is collimated with a lens 133, filtered with an optical filter 134, and focused with a lens 135 into an aperture of a detector 136. The detector 132 can be for example a photo-multiplier tube and the detector 136 can be for example a photo-diode. The detectors 132 and 136 are arranged to produce first and second detection signals responsive to the detected beam with the first emission wavelength and to the detected beam with the second emission wavelength. The first and second detection signals are then amplified and processed to achieve a value for the intensities of the emission beams with the first and second emission wavelengths.

In the AlphaScreen™ measurement mode, the excitation light beam is received from an excitation light source 137 that is a laser source. The excitation light beam is guided via an optical guide 138 to the dichroic mirror 125. In the AlphaScreen™ measurement only one detector 132 is used, preferably a photomultiplier tube. In the AlphaScreen™ measurement a transparent thermo plate (not shown) is preferably used for sealing the openings of the sample wells 161-167.

Figure 2:
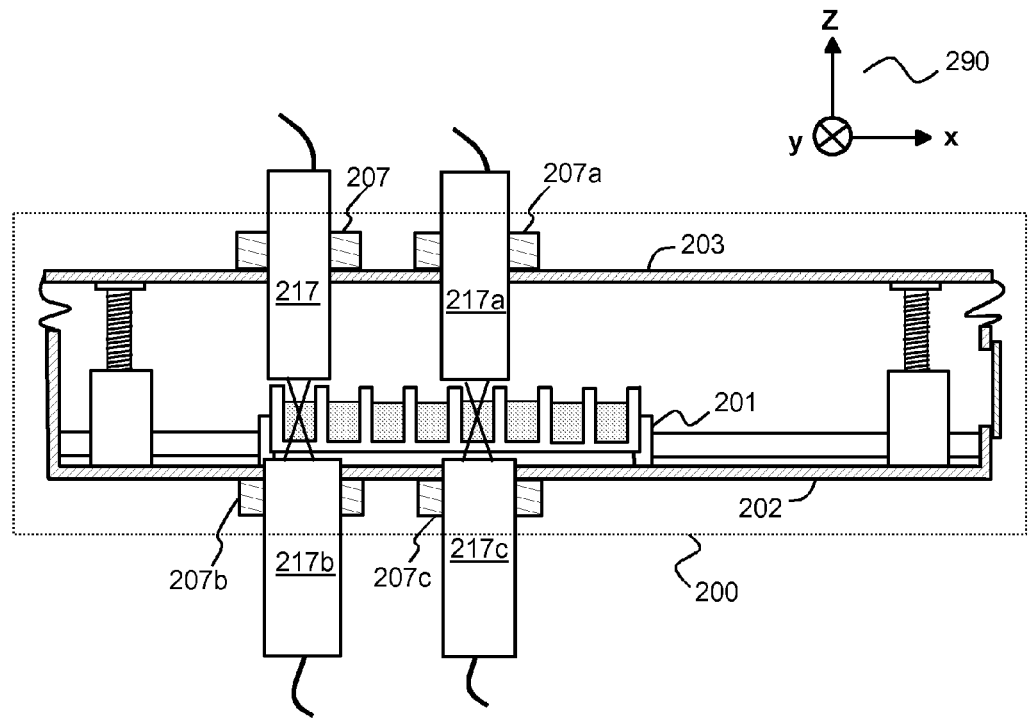

FIG. 2 shows a schematic illustration of a section view of an optical measurement instrument that comprises a body module 200 according to an embodiment of the invention. The optical measurement instrument allows simultaneous measurement of two samples. The body module comprises a first plate 202 and a second plate 203 that is substantially parallel and, in a direction perpendicular to the first plate, overlapping with the first plate. The second plate 203 is movably supported with respect to the first plate 202 so that the second plate is movable in the direction substantially perpendicular to the first and second plates, i.e. the second plate is moveable in the positive and negative z-directions of the co-ordinate system 290. The body module comprises walls extending from outer edges of the first plate to outer edges of the second plate. The second plate 203 comprises fastening interfaces 207 and 207a that are suitable for optical modules 217 and 217a that are mounted to the second plate, and the first plate 202 comprises fastening interfaces 207b and 207c that are suitable for optical modules 217b and 217c that are mounted to the first plate. The optical modules 217 and 217 may comprise, for example, optical elements for generating and directing excitations beams to the samples being currently measured, and the optical modules 217b and 217c may comprise, for example, detectors. The body module comprises a reception device 201 for receiving samples to be measured. The reception device and thus also the samples are movable in parallel with the first and second plates 202 and 203, i.e. in the xy-plane of the co-ordinate system 290. The distance from the optical modules 217 and 217a to the samples being measured can be adjusted by moving the second plate 203 in the positive or negative z-direction.

Figure 3:
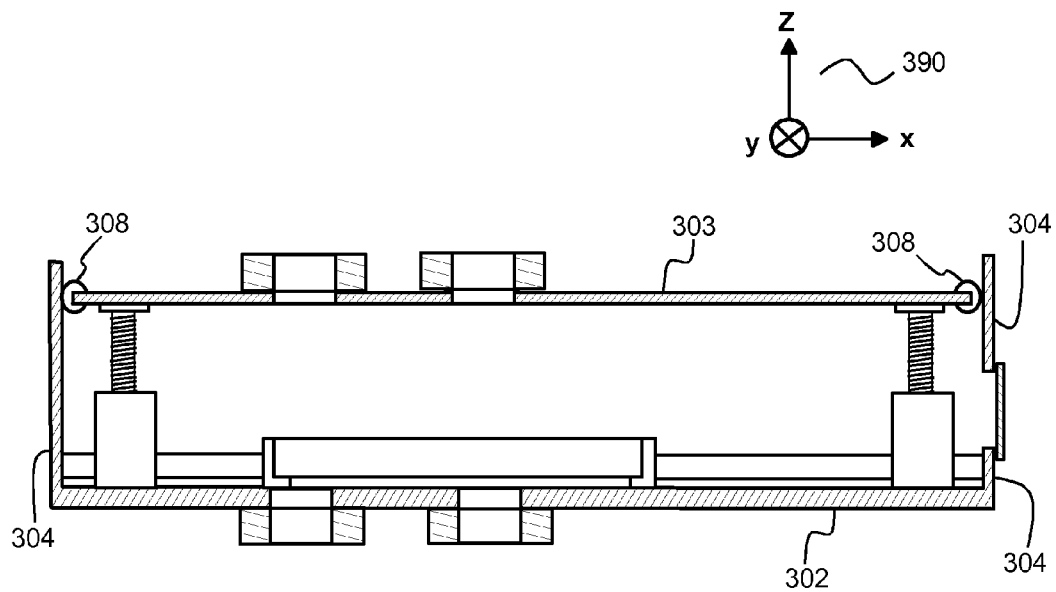
FIGS. 3-5 show schematic illustrations of section views of body modules according to embodiments of the invention.

FIG. 3 shows a schematic illustration of a section view of a body module according to an embodiment of the invention. The body module comprises a first plate 302, a second plate 303, and walls 304 extending from the outer edges of the first plate to the outer edges of the second plate. The walls 304 are fastened to the outer edges of the first plate 302 and the outer edges of the second plate 303 are provided with a seal 308 arranged slide along the walls in response to the movement of the second plate 303 relative to the first plate 302 in the positive or negative z-direction of the co-ordinate system 390.

Figure 4:
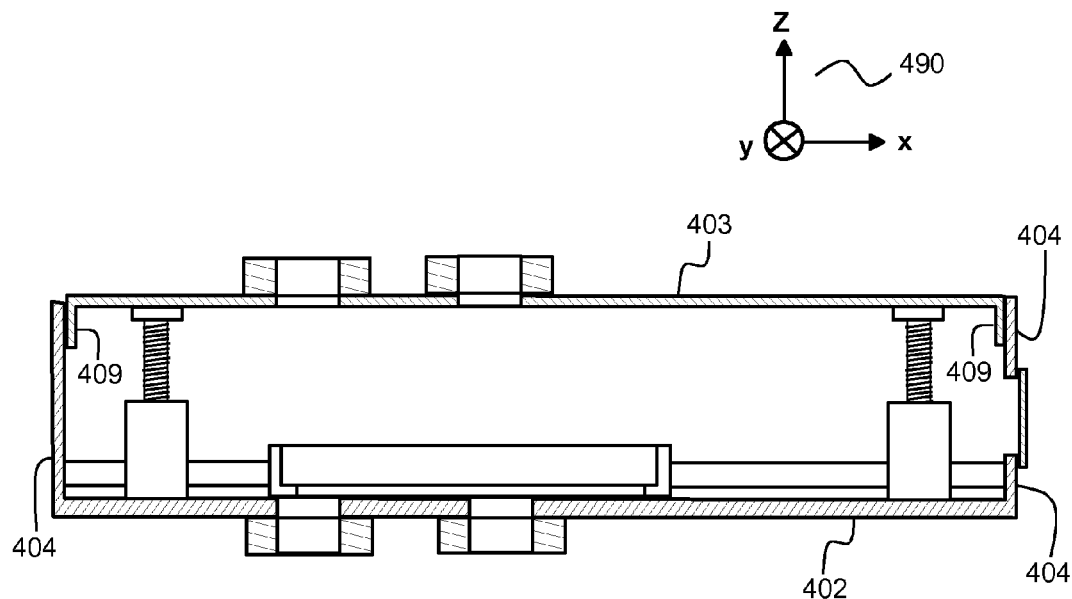

FIG. 4 shows a schematic illustration of a section view of a body module according to an embodiment of the invention. The body module comprises a first plate 402, a second plate 403, and walls extending from the outer edges of the first plate to the outer edges of the second plate. The walls comprise a first portion 404 fastened to the outer edges of the first plate 402 and a second portion 409 fastened to the outer edges of the second plate 403. The second portion 409 is arranged to slide relative to the first portion 404 in response to the movement of the second plate 403 relative to the first plate 402 in the positive or negative z-direction of the co-ordinate system 490.

Figure 5:
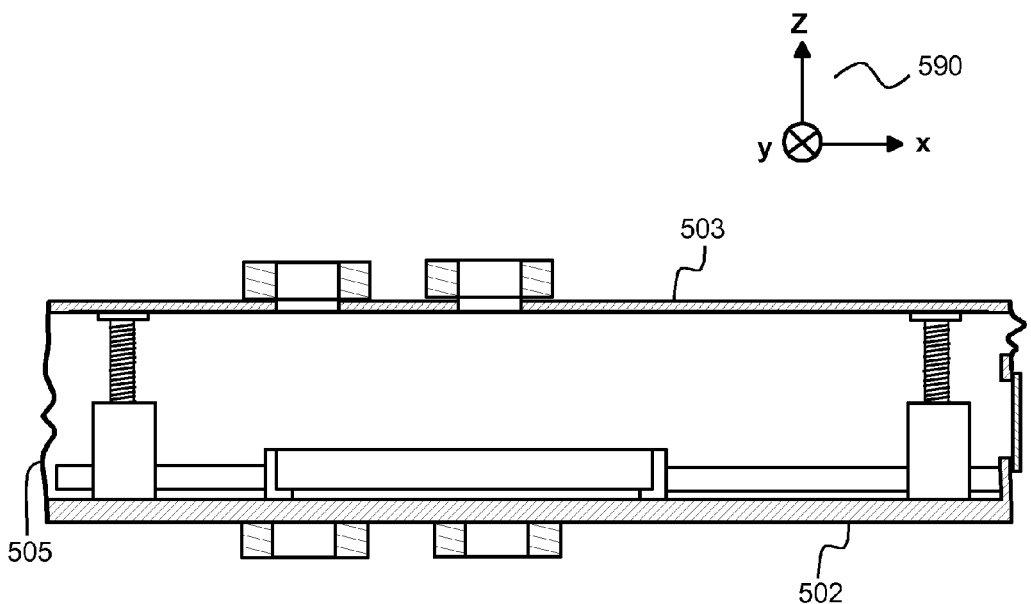

FIG. 5 shows a schematic illustration of a section view of a body module according to an embodiment of the invention. The body module comprises a first plate 502, a second plate 503, and walls extending from the outer edges of the first plate to the outer edges of the second plate. The walls comprise flexible material 505 fastened to the outer edges of the first plate 502 and to the outer edges of the second plate 503. The flexible material allows the movement of the second plate 503 relative to the first plate 502 in the positive or negative z-direction of the co-ordinate system 590.

Figure 6A:
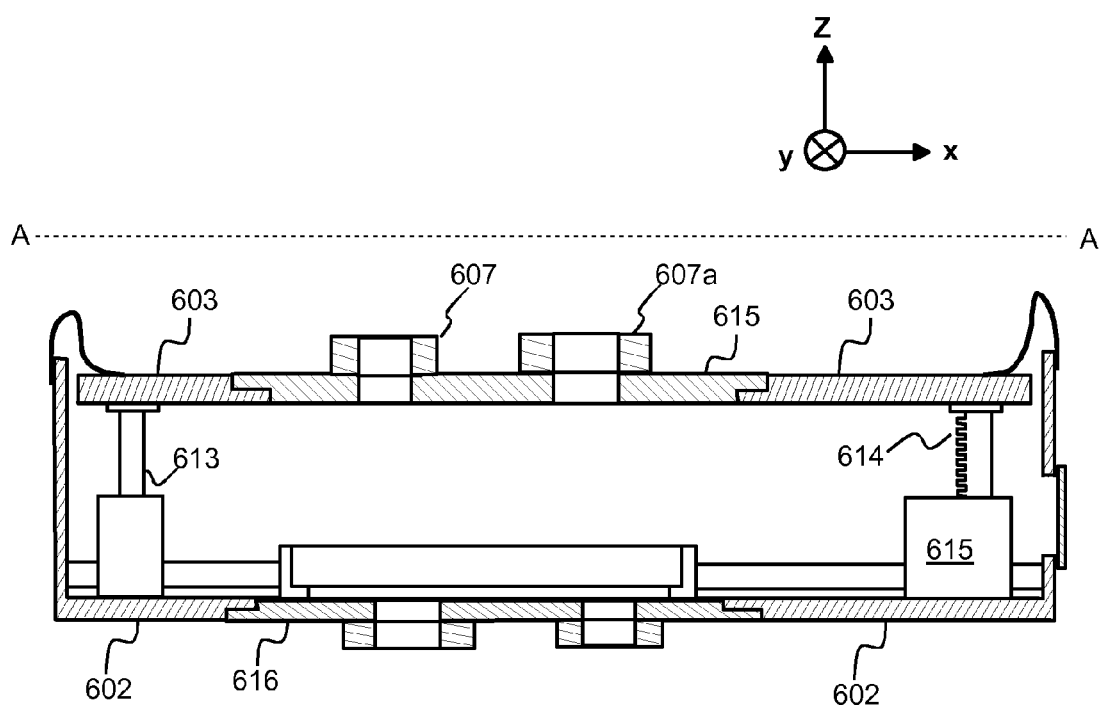
FIG. 6a shows a schematic illustration of a section view of a body module according to an embodiment of the invention.
Figure 6B:
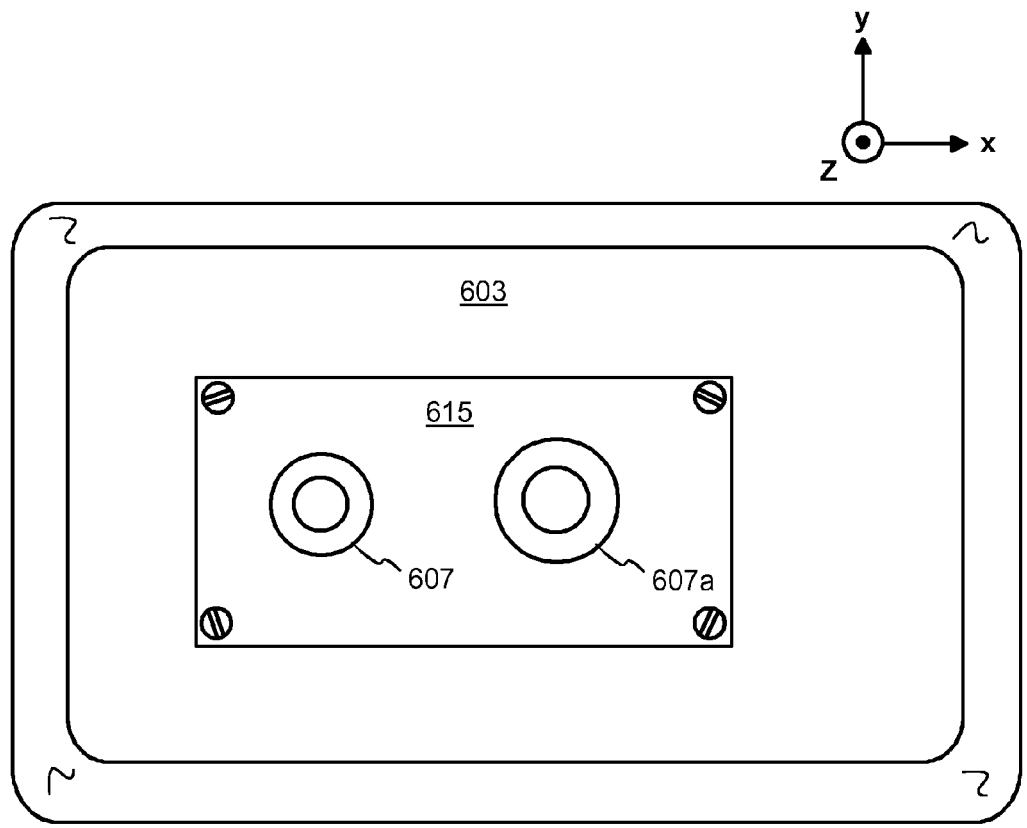

FIG. 6a shows a schematic illustration of a section view of a body module according to an embodiment of the invention. FIG. 6b shows a schematic illustration of a view seen downwards from line A-A of FIG. 6a. The body module comprises a first plate, a second plate, and walls extending from the outer edges of the first plate to the outer edges of the second plate. The second plate comprises a first part 603 the outer edges of which are in contact with the walls and a second part 615 that is detachably fastened to an opening of the first part. The second part 615 comprises one or more fastening interfaces 607 and 607b each of which being suitable for an optical module to be mounted to the second plate. Using different second parts 615 it is possible to use the same body module as a platform with the aid of which different optical measurement instruments can be constructed. The second plate is movably supported to the first plate with sliding elements 613 and with a toothed bar 614. An element 615 can be provided for example with a servomotor arranged to move the second plate.

In a body module according to an embodiment of the invention, the first plate comprises a first part 602 the outer edges of which are in contact with the walls and a second part 616 detachably fastened to an opening of the first part. The second part comprises one or more fastening interfaces suitable for one or more optical modules to be mounted to the first plate.

The specific examples provided in the description given above should not be construed as limiting. Therefore, the invention is not limited merely to the embodiments described above.

What is claimed is:

1. A body module for an optical measurement instrument, the body module comprising:
    a first plate,
    a second plate substantially parallel with the first plate and movably supported with respect to the first plate by mechanisms extending between the first and second plates, the second plate being movable in a direction substantially perpendicular to the first and second plates and comprising at least one fastening interface provided with an aperture and configured to support an optical module to be mounted thereto,
    walls extending from outer edges of the first plate to outer edges of the second plate, the walls and the first and second plates constituting a measurement chamber and the walls comprising a door element for enabling insertion of samples to be measured into the measurement chamber, and
    a reception device for receiving the samples to be measured, the reception device being located in the measurement chamber and being mechanically connected to a movable support rail so that the reception device is movable in a plane parallel with the first and second plates.

2. A body module according to claim 1, wherein the walls comprise flexible material fastened to the outer edges of the first plate and to the outer edges of the second plate, the flexible material allowing the movement of the second plate relative to the first plate.

3. A body module according to claim 1, wherein the walls are fastened to the outer edges of the first plate, and the outer edges of the second plate are provided with a seal arranged to slide along the walls in response to the movement of the second plate relative to the first plate.

4. A body module according to claim 1, wherein the walls comprise a rigid portion fastened to the outer edges of the first plate and a flexible portion fastened between the rigid portion and the outer edges of the second plate, the flexible portion allowing the movement of the second plate relative to the first plate.

5. A body module according to claim 1, wherein the walls comprise a first portion fastened to the outer edges of the first plate and a second portion fastened to the outer edges of the second plate, the second portion being arranged to slide relative to the first portion in response to the movement of the second plate relative to the first plate.

6. A body module according to claim 1, wherein the reception device comprises an interface for receiving a separate element including a plurality of sample wells.

7. A body module according to claim 1, wherein the reception device comprises a plurality of sample wells.

8. A body module according to claim 1, wherein the second plate is movably supported with respect to the first plate with at least one threaded rod.

9. A body module according to claim 1, wherein the second plate is movably supported with respect to the first plate with at least one toothed bar.

10. A body module according to claim 1, wherein the second plate comprises a first part the outer edges of which are in contact with the walls and a second part detachably fastened to an opening of the first part, the second part comprising the fastening interface suitable for the optical module to be mounted to the second plate.

11. A body module according to claim 1, wherein the first plate comprises at least one fastening interface provided with an aperture, the fastening interface being suitable for an optical module to be mounted to the first plate.

12. A body module according to claim 11, wherein the first plate comprises a first part the outer edges of which are in contact with the walls and a second part detachably fastened to an opening of the first part, the second part comprising the fastening interface suitable for the optical module to be mounted to the first plate.

13. An optical measurement instrument comprising optical modules, at least one of the optical modules including an excitation light source arranged to produce an excitation beam for at least one of samples to be measured, and at least one of the optical modules including a detector arranged to detect an emission beam emitted by one of the samples to be measured and to produce a detection signal responsive to the detected emission beam,
    wherein the optical measurement instrument further comprises a body module according to claim 1 and at least one of the optical modules is mounted to the second plate of the body module via the fastening interface, the at least one optical module mounted to the second plate being at least one of a part of a route of the excitation beam and a part of a route of the emission beam.

* * * * *